United States Patent
Chen et al.

(10) Patent No.: US 10,094,949 B2
(45) Date of Patent: Oct. 9, 2018

(54) HYDROCARBON DETERMINATION IN UNCONVENTIONAL SHALE

(71) Applicants: Jinhong Chen, Katy, TX (US); Jilin Zhang, Cypress, TX (US); Guodong Jin, Katy, TX (US); Terrence Quinn, The Woodlands, TX (US); Elton Frost, Jr., Spring, TX (US)

(72) Inventors: Jinhong Chen, Katy, TX (US); Jilin Zhang, Cypress, TX (US); Guodong Jin, Katy, TX (US); Terrence Quinn, The Woodlands, TX (US); Elton Frost, Jr., Spring, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 1554 days.

(21) Appl. No.: 13/663,790

(22) Filed: Oct. 30, 2012

(65) Prior Publication Data
US 2013/0234703 A1 Sep. 12, 2013

Related U.S. Application Data

(60) Provisional application No. 61/553,731, filed on Oct. 31, 2011.

(51) Int. Cl.
*G01V 3/00* (2006.01)
*G01V 3/32* (2006.01)
*G01N 24/08* (2006.01)

(52) U.S. Cl.
CPC ............. *G01V 3/32* (2013.01); *G01N 24/081* (2013.01)

(58) Field of Classification Search
CPC ................. G01V 3/32; G01N 24/081
USPC .................................................. 324/303, 307
See application file for complete search history.

(56) References Cited

U.S. PATENT DOCUMENTS

| | | | |
|---|---|---|---|
| 4,015,195 A | 3/1977 | Hoyer et al. | |
| 5,585,720 A * | 12/1996 | Edwards | 324/309 |
| 5,696,448 A | 12/1997 | Coates et al. | |
| 6,366,087 B1 * | 4/2002 | Coates et al. | 324/303 |
| 6,977,499 B2 | 12/2005 | Kiesl et al. | |
| 7,253,617 B1 * | 8/2007 | Chen et al. | 324/303 |
| 2004/0232362 A1 | 11/2004 | Prelewitz | |

(Continued)

OTHER PUBLICATIONS

Surface tension values of some common test liquids for surface energy analysis, Jan. 2013 (Jan. 2013) [retrieved on Jan. 14, 2013 (Jan. 14, 2013)]. Retrieved from the internet, URL:http://www.surface-tension.de/.

(Continued)

*Primary Examiner* — Rodney Fuller
(74) *Attorney, Agent, or Firm* — Cantor Colburn LLP

(57) ABSTRACT

An apparatus for identifying a fluid and locations of the fluid in a formation of shale having porous kerogen material and an inorganic matrix defining pores and micro-fractures includes: a carrier configured to be conveyed through a borehole penetrating the shale; a nuclear magnetic resonance (NMR) tool disposed at the carrier and configured to perform NMR measurements on the shale, the NMR measurements include a spectrum of transverse relaxation times; and a processor configured to receive NMR measurements on the shale performed by the NMR tool and to identify the fluid and locations of the fluid in the shale using the spectrum of transverse relaxation times.

15 Claims, 5 Drawing Sheets

(56) References Cited

U.S. PATENT DOCUMENTS

| | | | |
|---|---|---|---|
| 2004/0257074 A1* | 12/2004 | Appel et al. | 324/303 |
| 2005/0272158 A1 | 12/2005 | Galford et al. | |
| 2006/0273788 A1 | 12/2006 | Georgi et al. | |
| 2007/0079964 A1 | 4/2007 | Shpakoff et al. | |
| 2008/0120034 A1* | 5/2008 | Georgi et al. | 702/6 |
| 2008/0206887 A1* | 8/2008 | Chen et al. | 436/173 |
| 2009/0058416 A1* | 3/2009 | Blanz | 324/303 |
| 2009/0072824 A1 | 3/2009 | Romero | |
| 2009/0091320 A1 | 4/2009 | Flaum et al. | |
| 2009/0189604 A1 | 7/2009 | Romero | |
| 2009/0254283 A1 | 10/2009 | Jacobi et al. | |
| 2009/0255669 A1* | 10/2009 | Ayan et al. | 166/250.15 |
| 2010/0138157 A1* | 6/2010 | Sun et al. | 702/6 |
| 2010/0237860 A1* | 9/2010 | Hurlimann et al. | 324/303 |
| 2011/0066404 A1* | 3/2011 | Salazar-Tio et al. | 703/1 |
| 2011/0068788 A1* | 3/2011 | Minh | G01V 3/18 324/303 |
| 2011/0108283 A1 | 5/2011 | Srnka et al. | |
| 2011/0181279 A1* | 7/2011 | Srnka et al. | 324/307 |
| 2011/0234220 A1* | 9/2011 | Mitchell et al. | 324/303 |
| 2011/0282584 A1 | 11/2011 | Baez et al. | |
| 2012/0035851 A1* | 2/2012 | Romero | 702/8 |
| 2012/0065888 A1* | 3/2012 | Wu et al. | 702/8 |
| 2012/0095687 A1 | 4/2012 | Lecompte | |
| 2012/0192639 A1 | 8/2012 | Valenza et al. | |
| 2012/0192640 A1* | 8/2012 | Minh et al. | 73/152.16 |
| 2012/0232859 A1* | 9/2012 | Pomerantz et al. | 703/2 |
| 2012/0273193 A1* | 11/2012 | Sen | G01N 24/081 166/250.01 |
| 2013/0200890 A1 | 8/2013 | Hursan | |
| 2013/0234703 A1 | 9/2013 | Chen et al. | |

OTHER PUBLICATIONS

Gelb, et al. "Phase separation in confined systems" Rep. Prog. Phys. 62 (1999), 1573-1659. Printed in the UK. received Apr. 12, 1999. pp. 1-87.

Jilin Zhang, Jin-Hong Chen, Guodong Jin, Terrence Quinn and Elton Frost, Butane "Condensation in Kerogen Pores and in Smectite Clay: the NMR Relaxation and Comparison in Lab Study", International Symposium of the Society of Core Analysts held in Aberdeen, Scotland, UK, Aug. 27-30, 2012, pp. 1-6.

Jin-Hong Chen, Jilin Zhang, Guodong Jin, Terrence Quinn, and Elton Frost, Baker Hughes, Jacie Chen, "Capillary Condensation and NMR Relaxation Time in Unconventional Shale Hydrocarbon Resources", SPWLA 53rd Annual Logging Symposium, Jun. 16-20, 2012, pp. 1-9.

Lewis R, Ingraham D, Peracy M, Williamson J, Sawyer W, Frantz J, "New evaluation techniques for gas shale reservoirs", Reservoir Symposium 2004. pp. 1-11.

S. Brunauer, et al. "Adsorption of Gases in Multimolecular Layers", J. Am. Chem. Soc., Feb. 1938, 60, 309-319.

Shapiro, et al "Kelvin equation fora non-ideal multicomponent mixture". Fluid Phase Equilibria 134 (1997) 87-101.

Ambrose R.J., Hartman R.C. and Akkutlu I.Y., 2011, "Multicomponent sorbed-phase considerations for shale gas-in-place calculation", SPE 141416, SPE Production and Operations Symposium held in Oklahoma city, Oklahoma, USA Mar. 27-29, 2011. pp. 1-10.

Shapiro, et al. "Effects of Capillary Forces and Adsorption on Reserves Distribution". SPE European Petroleum Conference held in Milan, Italy, Oct. 22-24, 1996. pp. 441-448.

Shapiro, et al. "Effect of Low Permeable Porous Media on Behavior of Gas Condensates". SPE 65182, SPE European Petroleum Conference held in Paris, France, Oct. 24-25, 2000.

Thomson, "XLVI. Hydrokinetic Solutions and Observations". Sir W. Thomson on the motion of Free Solids through a Liquid. 1871. pp. 362-377.

Ambrose, et al. "New Pore-Scale Considerations for Shale Gas in Place Calculations", SPE 131772, SPE Unconventional Gas Conference, Pittsburgh, PA, Feb. 23-25, 2010, pp. 1-17.

Sondergeld, et al. ,"Petrophysical Considerations in Evaluating and Producing Shale Gas Resources", SPE 131768, SPE Unconventional Gas Conference, Pittsburgh, PA, Feb. 23-25, 2010, pp. 1-34.

LeCompte, et al. "Defining Clay Type Using NMR and Geochemical Logging Measurements", paper KKK, SPWLA 49th Annual Logging Symposium, Scotland, May 25-28, 2008. pp. 1-9.

Moss, et al. "Shale Volume Estimates from NMR Core Data", paper SCA2003-66, International Symposium of the Society of Core Analysts, Pau, France, Sep. 21-24, 2003, pp. 1-6.

Passey, Q. R., Bohacs, K. M., Esch, W. L., Klimenditis, R., and S. Sinha, 2010, "From Oil-Prone Source Rock to Gas-Producing Shale Reservoir Geologic and Petrophysical Characterization of Unconventional Shale-Gas Reservoirs" ExxonMobile, OGS New Perspectives on Shales—Jul. 28, 2010. 26 pages.

Prammer, et al. "Measurements of Clay-Bound Water and total Porosity by Magnetic Resonance Logging", SPE 36522, SPE Annual Technical confernce and Exhibition held in Denver, Colorado, USA Oct. 5-9, 1996, pp. 1-10.

Notification of Transmittal of the International Search Report and the Written Opinion of the International Searching Authority, or the Declaration; PCT/US2012/058513; Mar. 14, 2013

Notification of Transmittal of the International Search Report and the Written Opinion of the International Searching Authority, or the Declaration; PCT/US2013/060801; dated Dec. 26, 2013.

* cited by examiner

HYDROCARBON DETERMINATION IN UNCONVENTIONAL SHALE

CROSS REFERENCE TO RELATED APPLICATIONS

This application claims the benefit of an earlier filing date from U.S. Provisional Application Ser. No. 61/553,731 filed Oct. 31, 2011, the entire disclosure of which is incorporated herein by reference.

BACKGROUND

Although hydraulic fracturing and horizontal drilling are now routinely used to dramatically improve the production of gas from source shale (i.e., unconventional shale gas) and to make shale gas production commercially profitable, there is a fundamental need for understanding the rock and fluid physics of source shale. A clear understanding of the formation and the fluid (including gas) inside the formation is required to evaluate the production potential of the shale. Among all the logging technologies available for source shale evaluation, Nuclear Magnetic Resonance (NMR) provides an accurate porosity estimation along with information related to the fluids and gases within the rock.

The physical properties of source shale that defines the NMR response are the pore size and pore wettability. Source shale contains inorganic matrix, organic kerogen, and different fluids inside the pores. There are multiple types of porosities with diverse sizes and wettabilities which can be partitioned into three groups based on their origin. Pores within the kerogen are in the size of nanometer to 100 nanometers and are hydrocarbon wet. The pores inside the inorganic matrix are approximately the size of the rock grains themselves and are in the range of sub-microns. These pores are largely water wet to fractionally (mixed) wet. The third type of porosity is that of the micro-fractures which are larger than microns in size and are normally water wet or fractionally water wet. It would be well received in the drilling industry if apparatus and method could be developed to understand the nature of the fluids and gases in the shale gas rock and relate it to the NMR data that can be obtained using downhole NMR instruments.

BRIEF SUMMARY

An apparatus is disclosed for identifying a fluid and locations of the fluid in a formation of shale having porous kerogen material and an inorganic matrix defining pores and micro-fractures. The apparatus includes: a carrier configured to be conveyed through a borehole penetrating the shale; a nuclear magnetic resonance (NMR) tool disposed at the carrier and configured to perform NMR measurements on the shale, the NMR measurements include a spectrum of transverse relaxation times; and a processor configured to receive NMR measurements on the shale performed by the NMR tool and to identify the fluid and locations of the fluid in the shale using the spectrum of transverse relaxation times.

Also disclosed is a method for identifying a fluid and locations of the fluid in a formation of shale having porous kerogen material and an inorganic matrix defining pores and micro-fractures. The method includes: conveying a carrier through a borehole penetrating the formation; performing nuclear magnetic resonance (NMR) measurements on the formation using an NMR tool disposed at the carrier, the NMR measurements include a spectrum of transverse relaxation times; and identifying the fluid and locations of the fluid in the formation using the spectrum of transverse relaxation times.

Further disclosed is a non-transitory computer-readable medium having computer-executable instructions for identifying a fluid and locations of the fluid in a formation of shale having porous kerogen material and an inorganic matrix defining pores and micro-fractures by implementing a method. The method includes: receiving nuclear magnetic resonance (NMR) measurements of the formation using an NMR tool disposed at a carrier conveyed through a borehole penetrating the formation, the NMR measurements include a spectrum of transverse relaxation times; and identifying the fluid and locations of the fluid in the shale using the spectrum of transverse relaxation times.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the Figures.

Figure 1:
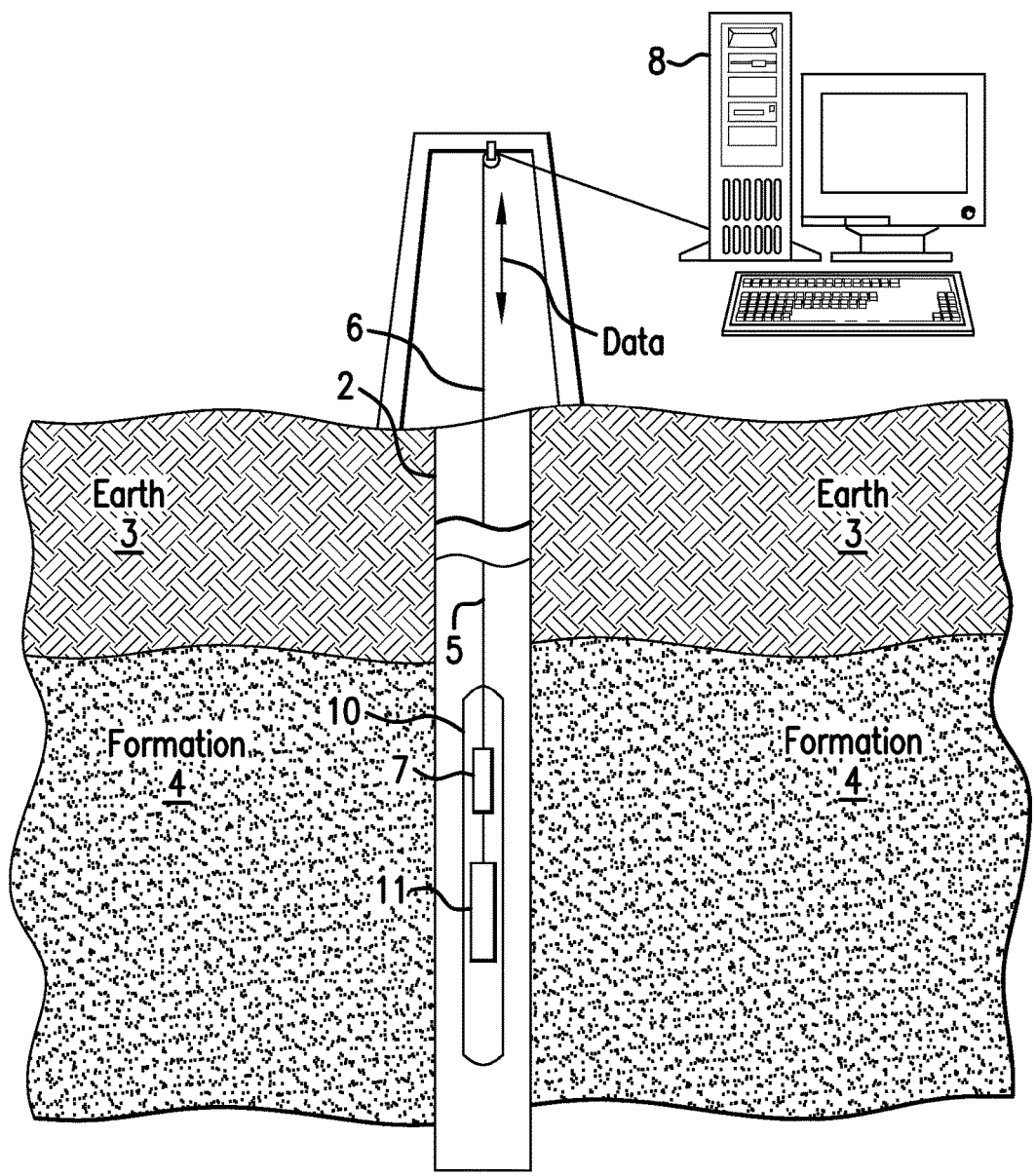
FIG. 1 illustrates an exemplary embodiment of a downhole NMR tool disposed in a borehole penetrating the earth.

FIG. 1 illustrates an exemplary embodiment of a nuclear magnetic resonance (NMR) tool 10 disposed in a borehole 2 penetrating the earth 3, which includes an earth formation 4 of source shale. The source shale, which may be referred to as unconventional shale, kerogen material and a matrix of inorganic material having pores and/or micro-fractures. The NMR tool 10 is conveyed through the borehole 2 by a carrier 5. In the embodiment of FIG. 1, the carrier 5 is an armored wireline 6. In addition to supporting the NMR tool 10 in the borehole 2, the wireline 6 can also provide communications between the downhole tool and a computer processing system 8 disposed at the surface of the earth 3. In logging-while-drilling (LWD) or measurement-while-drilling (MWD) embodiments, the carrier 5 can be a drill string. In order to operate the downhole tool 10 and/or provide a communications interface with the surface computer processing system 8, the downhole tool 10 includes downhole electronics 7. Downhole electronics 7 are configured to operate the tool 10 and/or process measurements or data received from the tool 10. NMR data processing or operations can also be performed by the computer processing system 8 in addition to or in lieu of the downhole electronics 7.

The NMR tool 10 includes NMR components 11 configured to perform NMR measurements on a sensitive volume in the formation 4. The NMR components 11 include a magnet arrangement that is used to generate a static magnetic field having a substantially uniform field strength in the sensitive volume in the formation surrounding the borehole. An RF coil or antenna is used to produce pulsed RF fields substantially orthogonal to the static field in the region of examination. The nuclear spins in the formation align themselves along the externally applied static magnetic field. A pulsed RF field is applied to tip the spins into the transverse plane, resulting in a precession of the spins. A tipping pulse is followed by a series of refocusing pulses and the resulting series of pulse echoes is detected by a receiver coil or antenna. The sequence of pulses is generally referred to as CPMG (Carr-Purcell-Meiboom-Gill). An alternative sequence may be used such as to maximize signal and minimize RF power consumption. The NMR signals include a longitudinal relaxation decay time constant (referred to as $T_1$) and a transverse relaxation decay time constant (referred to as $T_2$). As these NMR signals are known in the art, they are not discussed in further detail.

The conventional model of gas shale assumes the hydrocarbon in kerogen pores in the shale is in a gas states surrounded by one molecular layer of the hydrocarbon in a liquid state. A new model disclosed herein for gas shale assumes the hydrocarbon in kerogen pores is mostly all in a liquid state based on capillary condensation. Capillary condensation occurs only when, first, the pore surface is initially hydrocarbon wet and, second, the pore size and vapor pressure satisfy the Kelvin equation (Equation 1).

$$\ln \frac{P_v}{P_{sat}} = -\frac{2\sigma_{lg} V_L \cos\theta}{dRT} \quad (1)$$

In equation (1), $P_v$ is the vapor pressure, $P_{sat}$ is the saturation vapor pressure, $\sigma_{lg}$ is the surface tension between gas and liquid, $\theta$ is the pore surface wettability to the liquid, $V_1$ is the liquid molar density, d is the diameter of the cylinder, R is the gas constant, and T is the temperature. The kerogen pores are in the size of nanometer to 100 nanometers and are hydrocarbon wet, and as long as the Kelvin Equation is satisfied there is no gas state. However, gas may still exist in large pores. FIG. 1 depicts aspects of capillary condensation in a small pore represented by a cylinder.

Next, a laboratory technique is presented to selectively saturate kerogen pores with hydrocarbon liquid using capillary condensation and taking advantage of the wettability and size difference of kerogen pores and inorganic matrix pores. The nanometer size pores in kerogen can be selectively saturated by exposing them to hydrocarbon vapor, while the inorganic matrix is not saturated because the pore size is larger and not strongly hydrocarbon wet.

Figure 2:
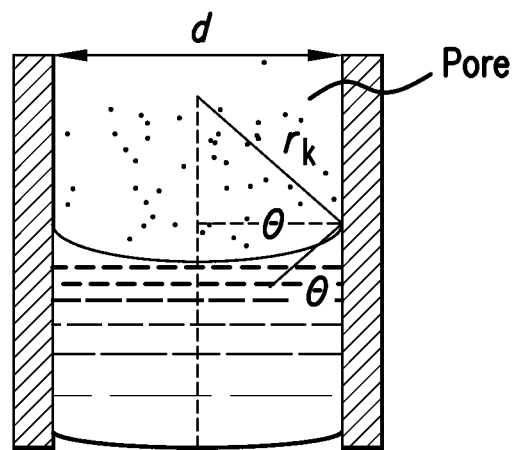
FIG. 2 depicts aspects of capillary condensation in a small pore.
Figure 3:
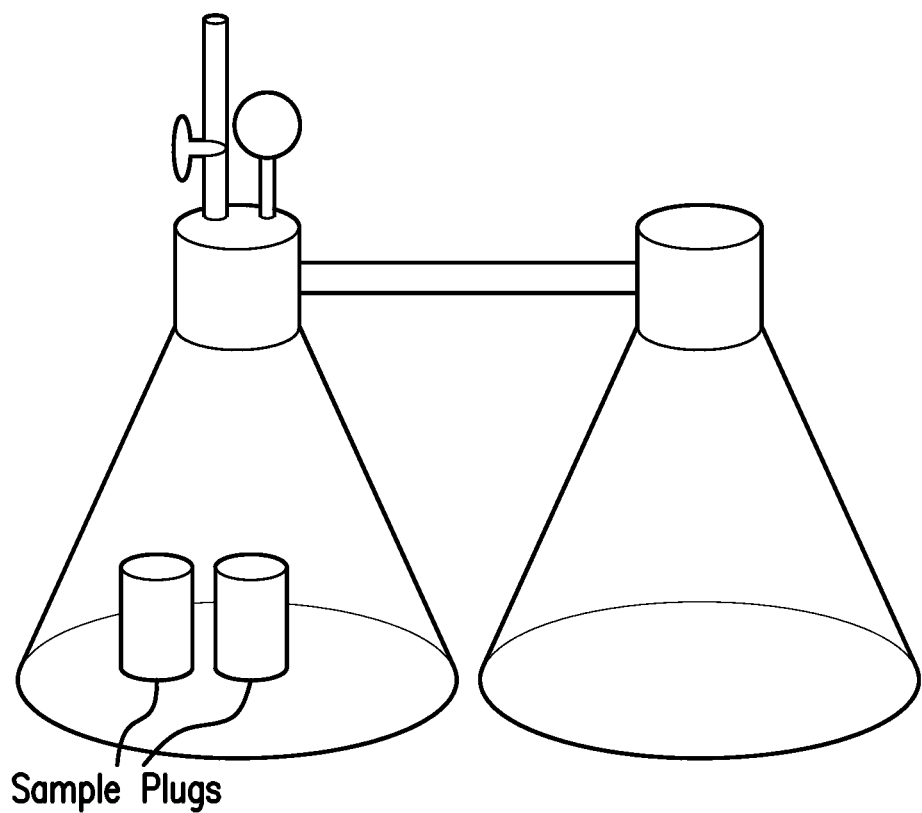
FIG. 3 depicts aspects of an experimental setting for saturation of kerogen pores using a light hydrocarbon based on capillary condensation.
Figure 4:
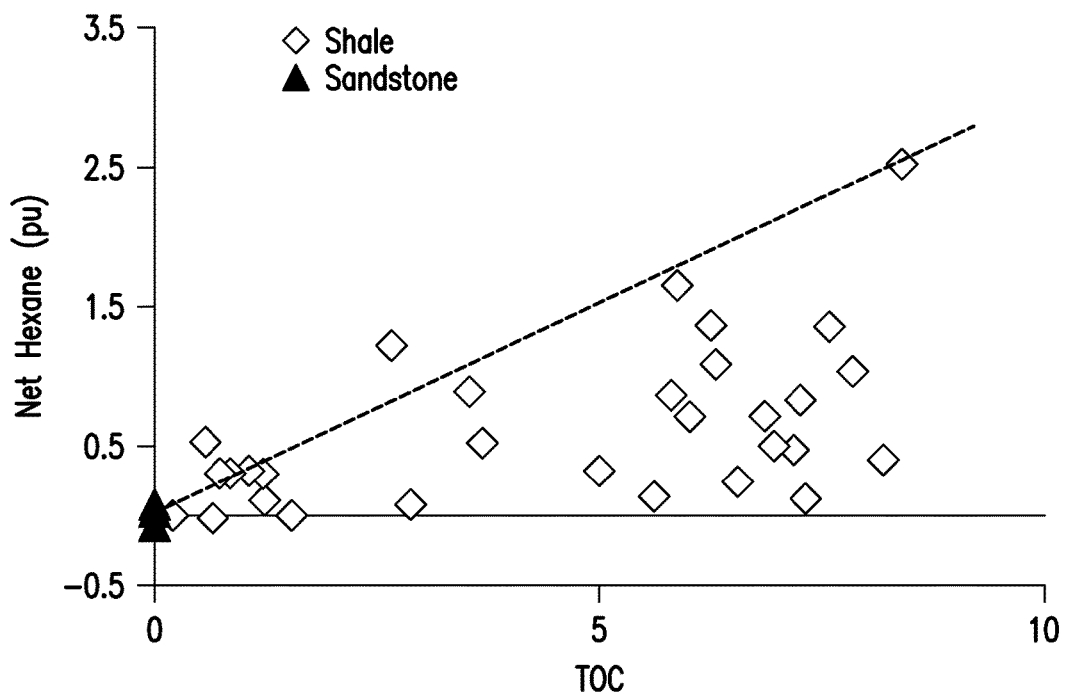
FIG. 4 depicts aspects experimental results of capillary condensation of hexane in source shale plugs and three sandstone plugs according to total organic content.

In one experiment, a sample is put in a vial, dried at 110° C. for 24 hours and cooled in vacuum. Hydrocarbon saturation of source shale plugs was done using the setting illustrated in FIG. 2. Samples were placed in an enclosed flask that was connected with an empty flask. When the flasks were vacuumed completely, hexane was injected into the empty flask through a rubber septum. In another experiment, butane was released into the flask through a valve. In case of butane, the initial pressure inside the flask was 1 bar after the injection of the butane and as adsorption occurred, the pressure dropped continually thus more butane was released into the vial. All experiments are done at the room temperature. FIG. 4 illustrates a plot of weight change according to the total organic content (TOC). Three sandstone plugs were also included in the experiments and showed no weight increase. The reason for no weight increase is that there is no hydrocarbon wet pores in these sandstone plugs. The net increase of hexane or butane in each plug was measured by weight change using a scale.

Figure 5:
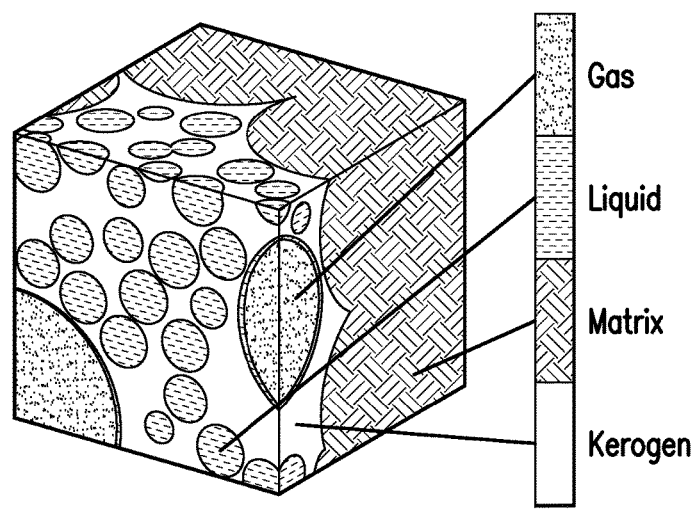
FIG. 5 depicts aspects of a hydrocarbon in kerogen pores.

FIG. 5 illustrates the new model depicting various states of hydrocarbon in kerogen pores. In small pores and throats between pores, hydrocarbon exists in the liquid state. Gas sate hydrocarbon can only be found in large pores. Based on this model, the moving of gas from one pore to another pore will be a multi-step of solving and dissolving processes.

Figure 6:
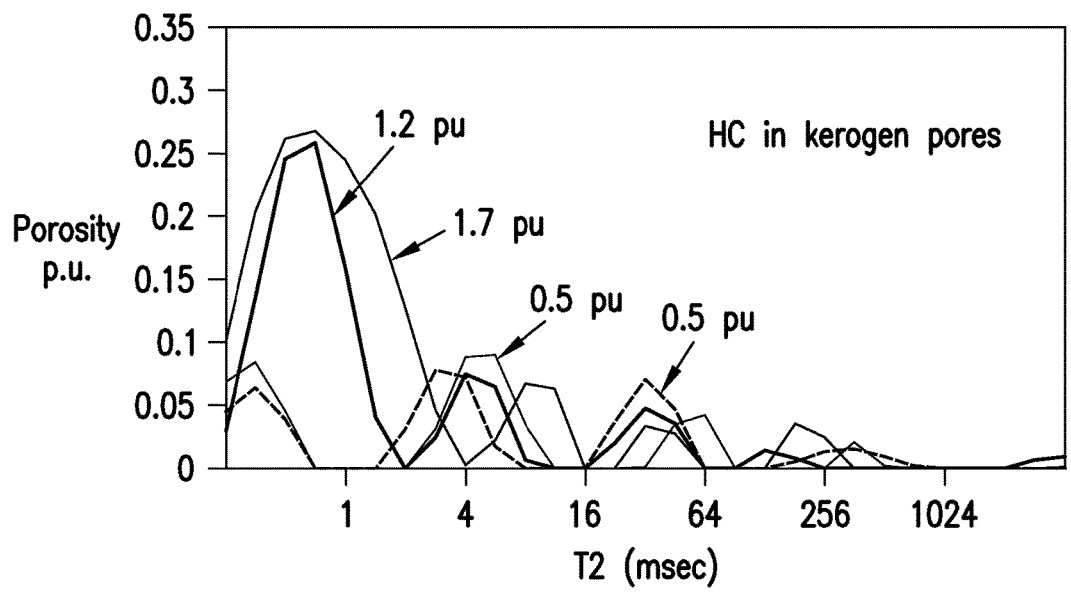
FIG. 6 depicts aspects NMR spectra of a hydrocarbon in kerogen pores acquired on plugs saturated by capillary condensation.

FIG. 6 illustrates the NMR spectra of the hydrocarbon in plugs having kerogen pores saturated using capillary condensation. The NMR measured porosity for each sample is consistent with the weight changes on FIG. 4.

Figure 7:
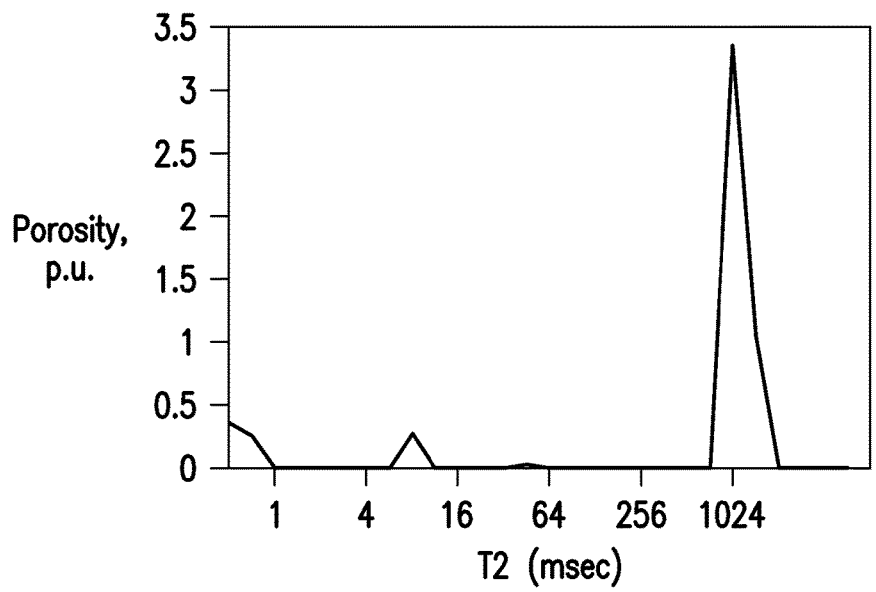
FIG. 7 depicts aspects of an NMR spectrum of hexane in water to neutral wet pores of porous glass beads.

FIG. 7 illustrates the NMR spectrum acquired on hexane in the nanometer pores of glass beads, which indicate that without strong surfacing wetting, the NMR relaxation decay time constant is much longer, in contrast to that of hydrocarbon in wetted pores as shown in FIG. 6.

It can be appreciated that by obtaining NMR measurements of source shale the type of liquid (e.g., hydrocarbon or water) and the locations of the liquid (e.g., kerogen pores, inorganic matrix pores or inorganic matrix micro-fractures) can be determined. Table 1 presents a summary of the pores inside of source shale and the expected NMR response obtained from experimentation.

TABLE 1

| Pore Type | Size | Wettability | Liquid In Pore | NMR $T_2$ |
|---|---|---|---|---|
| Pore in kerogen | ~80 nm | Hydrocarbons (HC) | HC | <10 ms |
| Pore in inorganic matrix | ~grain size <2 μm | Water Partially HC | Water HC | <3.3 ms ~1 sec. |
| Micro-fracture in inorganic matrix | <1 μm | Water/Partially HC | HC | ~100 ms |

In Table 1, the expected NMR $T_2$ response for hydrocarbon in inorganic matrix pores is approximately one second, which is in a range of 0.9 to 1.1 seconds. The expected NMR $T_2$ response for hydrocarbon in micro-fractures is about 100 milliseconds, which is in a range of 90 to 110 milliseconds.

It can be appreciated that more accurate and precise NMR responses can be obtained for specific hydrocarbons through further experimentation using those specific hydrocarbons.

It can be appreciated that an amount of liquid in the formation 4 may be estimated by integrating the transverse relaxation decay time constant ($T_2$) spectrum over time to give the percentage of liquid per volume of rock.

It can be appreciated that the NMR signals can also be used to detect a gas in the source shale. The detected NMR signals are in dynamic equilibrium with the liquid and the gas. By discriminating between the various NMR signals, the type of fluid and its state can be determined along with the locations (e.g., kerogen pores, inorganic matrix pores or inorganic matrix micro-fractures) of the fluid.

Figure 8:
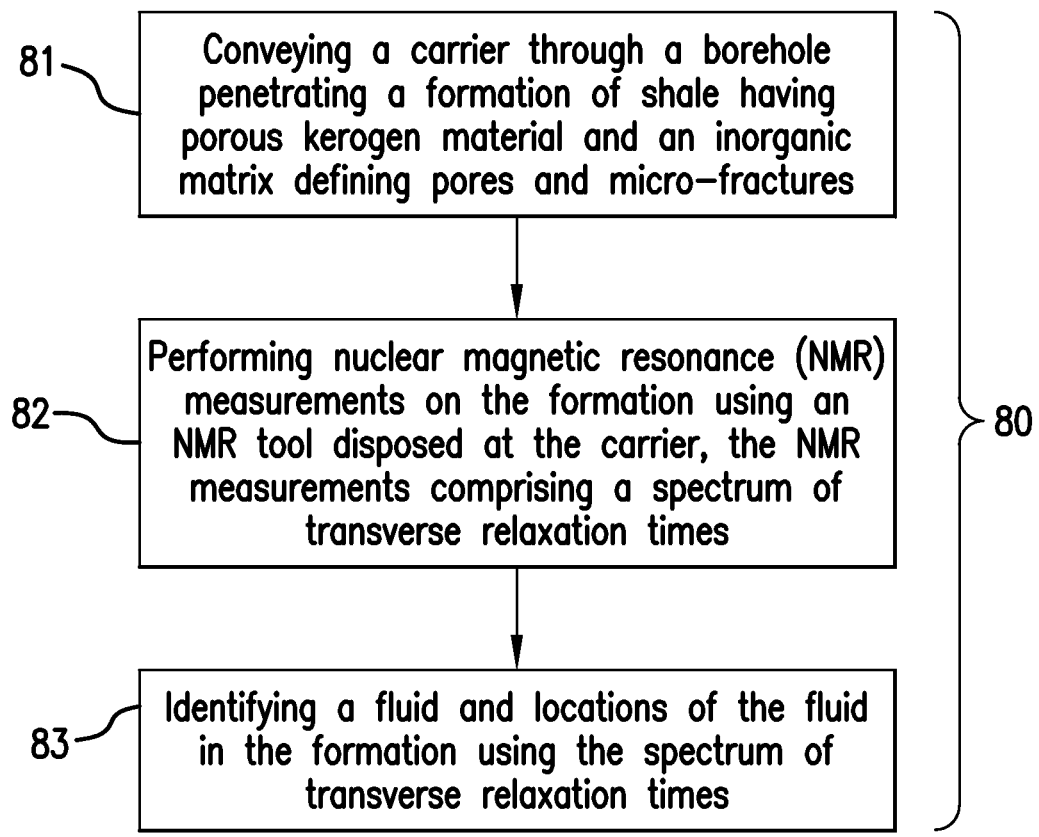
FIG. 8 presents one example of a method for identifying a liquid and locations of the liquid in a formation of shale comprising kerogen material and an inorganic matrix defining pores and micro-fractures.

FIG. 8 presents one example of a method 80 for identifying a fluid and locations of the fluid in a formation of shale having porous kerogen material and an inorganic matrix defining pores and micro-fractures. The fluid can be in a liquid state or a gaseous state. The method 80 calls for (step 81) conveying a carrier through a borehole penetrating the formation. Further, the method 80 calls for (step 82) performing nuclear magnetic resonance (NMR) measurements on the formation using an NMR tool disposed at the carrier, the NMR measurements comprising a spectrum of transverse relaxation times. Further, the method 80 calls for (step 83) identifying the fluid and locations of the fluid in the formation using the spectrum of transverse relaxation times.

In support of the teachings herein, various analysis components may be used, including a digital and/or an analog system. For example, the downhole electronics 7 or the surface computer processing 8 may include the digital and/or analog system. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for identifying a fluid and locations of the fluid in a formation of shale comprising porous kerogen material and an inorganic matrix defining pores and micro-fractures, the apparatus comprising:
    a carrier configured to be conveyed through a borehole penetrating the shale comprising porous kerogen material and an inorganic matrix defining pores and micro-fractures;
    a nuclear magnetic resonance (NMR) tool disposed at the carrier and configured to perform NMR measurements on the shale comprising porous kerogen material and an inorganic matrix defining pores and micro-fractures, the NMR measurements comprising a spectrum of transverse relaxation times; and
    a processor configured to receive NMR measurements on the shale comprising porous kerogen material and an inorganic matrix defining pores and micro-fractures performed by the NMR tool and to identify the fluid and locations of the fluid in the shale comprising porous kerogen material and an inorganic matrix defining pores and micro-fractures using the spectrum of transverse relaxation times.

2. The apparatus according to claim 1, wherein the fluid is hydrocarbon material; and the hydrocarbon material is present in pores in the kerogen material in the shale.

3. The apparatus according to claim 2, wherein a maximum peak of amplitude of the spectrum occurs at less than ten milliseconds transverse relaxation time.

4. The apparatus according to claim 3, wherein the processor is further configured to estimate a percentage of the hydrocarbon material by total volume of the shale by integrating the spectrum over time.

5. The apparatus according to claim 1, wherein the fluid is water disposed in pores of the inorganic matrix in the shale.

6. The apparatus according to claim 5, wherein a maximum peak of amplitude of the spectrum occurs at less than 3.3 milliseconds transverse relaxation time.

7. The apparatus according to claim 6, wherein the processor is further configured to estimate a percentage of the water by total volume of the shale by integrating the spectrum over time.

8. The apparatus according to claim 1, wherein the fluid is liquid hydrocarbon material disposed in pores in the inorganic matrix in the shale.

9. The apparatus according to claim 8, wherein a maximum peak of amplitude of the spectrum occurs at less than one second transverse relaxation time.

10. The apparatus according to claim 9, wherein the processor is further configured to estimate a percentage of the hydrocarbon material by total volume of the shale by integrating the spectrum over time.

11. The apparatus according to claim 8, wherein a maximum peak of amplitude of the spectrum is in a range of 20 to 200 milliseconds transverse relaxation time.

12. The apparatus according to claim 11, further comprising estimating a percentage of the hydrocarbon material by total volume of the shale by integrating the spectrum over time.

13. The apparatus according to claim 1, wherein the fluid is liquid hydrocarbon material disposed in the micro-fractures in the shale.

14. The apparatus according to claim 1, wherein carrier comprises a wireline, a slickline, a drill string or coiled tubing.

15. The apparatus according to claim 1, wherein pores of the porous kerogen material range in size from a nanometer to 100 nanometers.

* * * * *